United States Patent
Erbe et al.

(10) Patent No.: US 7,189,263 B2
(45) Date of Patent: Mar. 13, 2007

(54) BIOCOMPATIBLE BONE GRAFT MATERIAL

(75) Inventors: Erik M. Erbe, Berwyn, PA (US); Theodore D. Clineff, Phoenixville, PA (US); Charanpreet S. Bagga, Phoenixville, PA (US); Gina M. Nagvajara, Narberth, PA (US); Antony Koblish, Malvern, PA (US)

(73) Assignee: Vita Special Purpose Corporation, Wilmington, DE (US)

( * ) Notice: Subject to any disclaimer, the term of this patent is extended or adjusted under 35 U.S.C. 154(b) by 0 days.

(21) Appl. No.: 10/771,077

(22) Filed: Feb. 3, 2004

(65) Prior Publication Data
US 2005/0169956 A1    Aug. 4, 2005

(51) Int. Cl.
*A61F 2/28* (2006.01)

(52) U.S. Cl. .............................. 623/23.51; 623/16.11; 623/23.53; 623/23.54; 623/23.61; 424/422; 424/484; 424/602; 514/2; 514/801

(58) Field of Classification Search ............. 623/16.11, 623/23.54, 23.58, 23.61, 926; 424/423, 426, 424/484, 486
See application file for complete search history.

(56) References Cited

U.S. PATENT DOCUMENTS

| | | | | |
|---|---|---|---|---|
| 4,795,467 A | * | 1/1989 | Piez et al. ................... 424/423 |
| 5,238,491 A | * | 8/1993 | Sugihara et al. ............... 106/35 |
| 5,290,289 A | * | 3/1994 | Sanders et al. ................ 606/61 |
| 5,939,039 A | | 8/1999 | Sapieszko et al. ........... 423/311 |
| 5,964,809 A | * | 10/1999 | Lin et al. ..................... 264/257 |
| 6,325,987 B1 | | 12/2001 | Sapieszko et al. ........... 423/305 |
| 6,383,519 B1 | | 5/2002 | Sapieszko et al. ........... 424/489 |
| 6,458,162 B1 | * | 10/2002 | Koblish et al. ........... 623/23.51 |
| 6,521,246 B2 | | 2/2003 | Sapieszko et al. ........... 424/423 |
| 7,156,880 B2 | | 1/2007 | Evans et al. ............. 623/23.51 |
| 7,166,133 B2 | | 1/2007 | Evans et al. ............. 623/23.51 |
| 2002/0127720 A1 | * | 9/2002 | Erbe et al. ................... 435/395 |
| 2003/0180344 A1 | | 9/2003 | Wise et al. ................. 424/423 |

OTHER PUBLICATIONS

Bachand, WR, "Synthetic Osseous Grafting Materials: A Literature Review," http://das.cs.amedd.army.mil/journal/J9712.HTM accessed Mar. 4, 2005.*
Cornell et al, J Orthopaedic Trauma, 1991, vol. 5, No. 1, pp. 1-8.*
Kingery, W.D., Introduction to Ceramics, Wiley Series on the Science and Technology of Materials, 1st Ed., Hollowmon, J.H., et al. (Eds.), *Wiley & Sons*, 1960, 13.2, 409-417.

* cited by examiner

*Primary Examiner*—Leon B. Lankford, Jr.
*Assistant Examiner*—Allison M. Ford
(74) *Attorney, Agent, or Firm*—Woodcock Washburn LLP

(57) ABSTRACT

Biocompatible bone graft material having a biocompatible, resorbable polymer and a biocompatible, resorbable inorganic material exhibiting macro, meso, and microporosities.

27 Claims, 14 Drawing Sheets

BIOCOMPATIBLE BONE GRAFT MATERIAL

FIELD OF THE INVENTION

This invention relates to biocompatible bone graft materials for repairing bone defects and the application of the bone graft materials disclosed herein. The present invention incorporates the benefits of inorganic shaped bodies having macro, meso, and microporosity and polymers such as collagen.

BACKGROUND OF THE INVENTION

There has been a continuing need for improved bone graft materials. Although autograft, the current gold standard, has the ideal properties and radiopacity, the use of autogenous bone exposes the patient to a second surgery, pain, and morbidity at the donor site. Allograft devices, which are processed from donor bone, also have ideal radiopacity, but carry the risk of disease transmission. The devices are restricted in terms of variations on shape and size and have sub-optimal strength properties that decrease after implantation. The quality of the allograft devices varies because they are natural. Also, since companies that provide allograft implants obtain their supply from donor tissue banks, there tend to be limitations on supply. In recent years, synthetic materials have become a viable alternative to autograft and allograft devices. One such synthetic material is Vitoss® Scaffold Synthetic Cancellous Bone Void Filler (Orthovita, Inc., Malvern, Pa., assignee of the present application). Synthetic graft materials, like autograft and allograft, serve as osteoconductive scaffolds that promote the ingrowth of bone. As bone growth is promoted and increases, the graft material resorbs and is eventually replaced with new bone.

Many synthetic bone grafts include materials that closely mimic mammalian bone, such as compositions containing calcium phosphates. Exemplary calcium phosphate compositions contain type-B carbonated hydroxyapatite [$Ca_5(PO_4)_{3-x}(CO_3)_x(OH)$], which is the principal mineral phase found in the mammalian body. The ultimate composition, crystal size, morphology, and structure of the body portions formed from the hydroxyapatite are determined by variations in the protein and organic content. Calcium phosphate ceramics have been fabricated and implanted in mammals in various forms including, but not limited to, shaped bodies and cements. Different stoichiometric compositions such as hydroxyapatite (HAp), tricalcium phosphate (TCP), tetracalcium phosphate (TTCP), and other calcium phosphate salts and minerals, have all been employed to match the adaptability, biocompatibility, structure, and strength of natural bone. The role of pore size and porosity in promoting revascularization, healing, and remodeling of bone has been recognized as a critical property for bone grafting materials. The preparation of exemplary porous calcium phosphate materials that closely resemble bone have been disclosed, for instance, in U.S. Pat. Nos. 6,383,519 and 6,521,246, incorporated herein by reference in their entirety.

There has been a continued need for improved bone graft systems. Although calcium phosphate bone graft materials are widely accepted, they lack the strength, handling and flexibility necessary to be used in a wide array of clinical applications. Heretofore, calcium phosphate bone graft substitutes have been used in predominantly non-load bearing applications as simple bone void fillers and the like. For more clinically challenging applications that require the graft material to take on load, bone reconstruction systems that pair a bone graft material to traditional rigid fixation systems are used. The prior art discloses such bone reconstruction systems. For instance, MacroPore OS™ Reconstruction System is intended to reinforce and maintain the relative position of weak bony tissue such as bone graft substitutes or bone fragments from comminuted fractures. The system is a resorbable graft containment system composed of various sized porous sheets and sleeves, non-porous sheets and sleeves, and associated fixation screws and tacks made from polylactic acid (PLA). However, the sheets are limited in that they can only be shaped for the body when heated.

The Synthes SynMesh™ consists of flat, round, and oval shaped cylinders customized to fit the geometry of a patient's anatomical defect. The intended use is for reinforcement of weak bony tissue and is made of commercially pure titanium. Although this mesh may be load bearing, it is not made entirely of resorbable materials that are flexible.

There is a need for resorbable bone grafts with improved handling, which are flexible and not brittle, and are compression resistant. It has been discovered that admixing highly porous resorbable inorganic bodies with resorbable polymeric materials greatly improves upon handling, yet still provides an osteoconductive implant with good resorption and bone formation properties. It will be appreciated that such an implant would offer an easy-to-use dose of composite material and would be an advancement over current bone reconstruction systems for certain clinical applications in that it eliminates the need to have both a graft material and rigid fixation system.

It is an object of this invention to provide biocompatible graft materials with exceptional osteoconductive properties.

It is also an object of this invention to provide pre-sized graft materials in a variety of forms, including strips and cylinders for restoring defects in bone.

It is another object of this invention to provide bone graft materials that can be shaped.

It is another object of this invention to provide bone graft materials with improved handling properties, so that the graft material can be cut dry or after being wetted and does not crumble.

It is yet another object of this invention to provide bone graft materials with some compression resistance, such that the brittleness often associated with inorganic or ceramic bone graft materials is eliminated.

It is yet another object of this invention to provide bone graft materials with integrity that are at least partially load bearing.

It is yet another object of this invention to provide bone graft materials with improved pliability that still retain high degrees of porosity over a broad pore size distribution to maintain superior resorption and bone ingrowth properties.

It is yet another object of the invention to provide bone graft materials with fluid wicking and retention properties even under compressive loads.

It is a further object of this invention to provide bone grafts that provide easy implantation into a bony space and with decreased tendency to wash away when imbibed with fluid.

Additional objects, advantages, and novel features of this invention will become apparent to those skilled in the art upon examination of the following descriptions, figures and claims thereof, which are not intended to be limiting.

SUMMARY OF THE INVENTION

The present invention is directed to biocompatible bone graft materials that comprise a biocompatible, resorbable polymer and the oxidation-reduction reaction product of at least one metal cation, at least one oxidizing agent, and at least one oxidizable precursor anion. Suitable polymers may include structural proteins such as collagen. The reaction product may be selected to suit the needs of one skilled in the art but may be inorganic compositions comprising calcium phosphate, biphasic calcium phosphate, or beta tri-calcium phosphate (β-TCP).

The present invention is an improvement upon the shaped bodies disclosed in U.S. Pat. No. 6,383,519 ("'519 patent") and U.S. Pat. No. 6,521,246 ("'246 patent"), and the RPR process disclosed in U.S. Pat. No. 5,939,039 ("'039 patent") and U.S. Pat. No. 6,325,987 ("'987 patent"), all assigned to the present assignee and incorporated herein by reference in their entirety. The oxidation-reduction reaction product of the present invention shares the same unique porosity of those shaped bodies of the '519 and '246 patents. The reaction product grants the present invention graft material macro, meso, and microporosity, which allow the graft material to have extraordinary imbibation and absorption properties. Further, the inclusion of a polymer in the present invention material lends improved handling and flexibility. The graft materials can have a finite shape for some applications and are compression resistant or at least partially load bearing. When imbibed with fluids, the bone graft materials are flexible, bendable/deformable, and scalpable, without crumbling or falling apart. Some embodiments have a mesh or plate affixed to the bone graft material for added support. The bone graft materials may be imbibed with fluids such as bone marrow aspirate, blood, or saline. The graft materials may be provided in any basic shape, including cylinders, blocks, strips, sheets, and wedges. In one embodiment, the graft materials are provided in basic cylinder or strip form. In other embodiments, the graft materials may have a finite shape or custom shape for specific applications (e.g., semi-spherical for graft acetabular containment, half-tubular long bone wrap or sleeve), or may be "shredded" and housed within a delivery vessel. Yet, in other embodiments, the graft materials may serve as a coating on any orthopaedic appliance such as an intermedullary rod, pedicle screw, plate, hip stem, acetabular cup component and the like. The bone graft materials of the present invention also have the ability to attach to Bone Morphogenic Proteins (BMP).

This invention gives rise to biocompatible, resorbable composites that may have up to about 30% by weight of the biocompatible polymer and 70% by weight of the reaction product. The amount of biocompatible polymer within the bone graft materials may also be up to about 20% by weight or up to about 10% by weight, or alternatively up to about 50% by weight.

Figure 1A:
FIG. 1A illustrates one basic form of the biocompatible graft material in cylinder form.
Figure 1B:
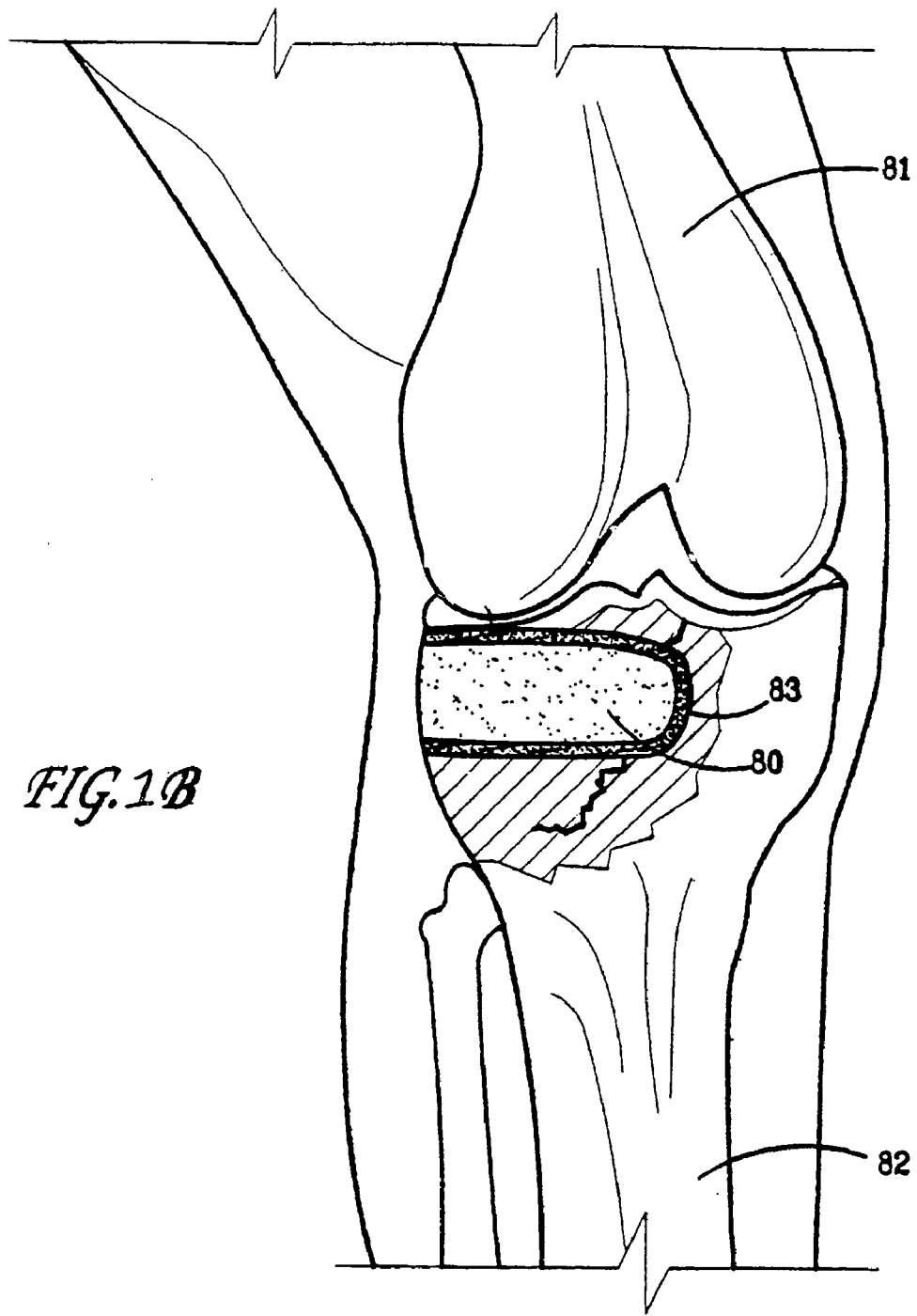
FIG. 1B depicts the graft material in cylindrical form 80 inserted into a bone void 83 below the femur 81 in the tibial plateau 82 within a human knee.
Figure 2:
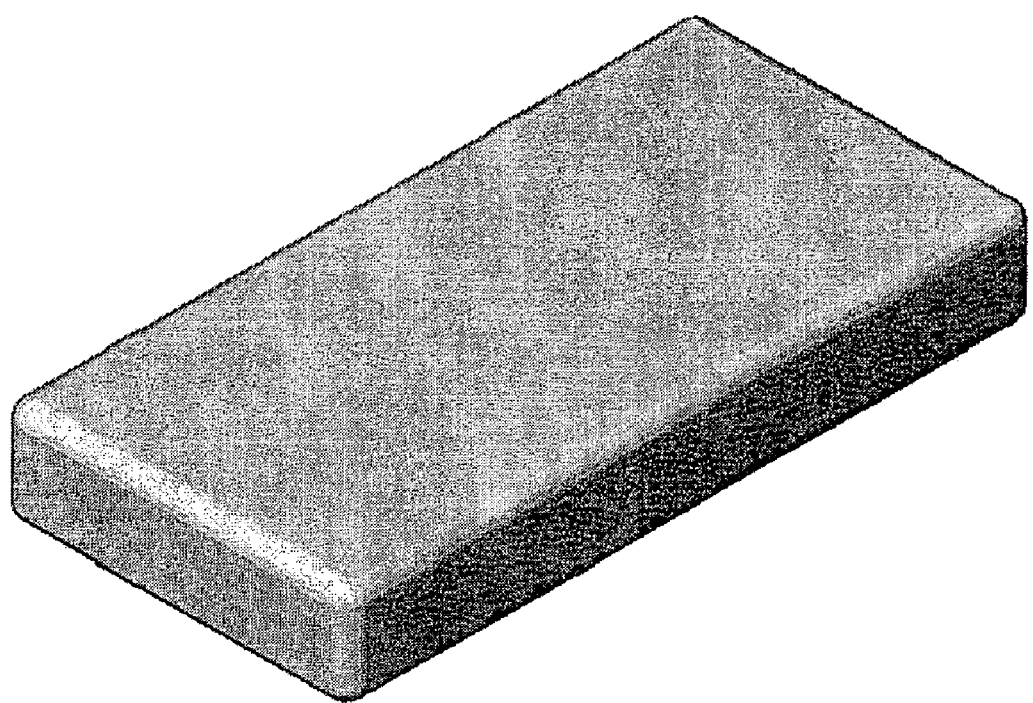
FIG. 2 illustrates another basic form of the present invention in strip form.

In accordance with the present invention, graft materials are provided comprising a biocompatible polymer such as collagen, the oxidation-reduction reaction product of at least one metal cation, at least one oxidizing agent, and at least one oxidizable precursor anion. Graft materials are also provided that comprise a collagen and macro-, meso-, and microporous calcium phosphate. Some embodiments may comprise up to 100% Type I collagen. In other embodiments, the collagens used may be predominantly, or up to about 90%, of Type I collagen with up to about 5% of Type III collagen or up to about 5% of other types of collagen. The Type I bovine collagen may be native fibrous insoluble collagen, soluble collagen, reconstituted collagen, or combinations thereof. The biocompatible polymer may be combined with the reaction product in slurry form, or combined by blending or kneading, to form a substantially homogenous mixture. As used in this context, substantially homogenous means that the ratio of components within the mixture is the same throughout. This, upon treatment using various preferred freeze-drying and crosslinking techniques, produces a form of the present invention graft material that may be preferred.

Collagen has been found to be particularly suitable in the present invention for service as the biocompatible polymer. The admixture of the collagen with the highly porous reaction product results in a graft that is highly porous with a broad pore size distribution, increased handling properties, and pliability beyond that which is achievable with some forms of the reaction product alone, for instance calcium phosphate. The resorption profile of some of the embodiments of the present invention may vary depending upon the amount, nature, and source of the collagen or other polymer used. Typically, by twelve weeks in vivo about 85%–95% of the present invention is resorbed. One reason that may explain the superior resorption properties of the present invention is the high degree of porosity retained even upon admixing the collagen with the reaction product. The collagen may be in a polymerized fibrous form that has a long three-dimensional architecture with multiple cross-links.

Preferable collagens have beneficial biochemical attributes such as 10% to 20% nitrogen, 10% to 15% of hydroxyproline, or up to 2.5% of ash content. In some embodiments, the collagens may be 10.5% to 17% nitrogen, 10.5% to 14% of hydroxyproline, or up to 2.5% of ash content. The percent nitrogen of a collagen is a measurement of nitrogen in a sample. In the presence of sulfuric acid, the amino nitrogen of organic material is converted to ammonium sulfate. The ammonium sulfate is distilled from an alkaline medium, and further decomposes from which the ammonia is absorbed into a boric acid solution containing a pH indicator. The ammonia (nitrogen) concentration determined calorimetrically by back titrating the boric acid solution with a standard acid.

The percent hydroxyproline of a collagen is a measure of hydroxyproline in a sample. Collagen is hydrolyzed with dilute Hydrochloric Acid, filtered and diluted. The solution is reacted with several reagents and then measured using ultraviolet (UV)/Vis analysis along with a standard hydroxyproline solution. Using the sample and standard absorbances, the percentage of hydroxyproline can be calculated [(Sample Abs)(Std)(Weight)(dilution factor)]/[(Sample weight)(Std. Abs)(dilution factor)].

The ash content of collagen is a measure of the amount of residual elements in collagen materials. When collagen is heated to extremely high temperatures, it is converted to mainly carbon dioxide and water. Elements other than collagen and hydrogen are converted to oxides and salts. A small sample of material is heated until there is only ash left. The weight of this ash is considered the gross amount of inorganic/organic material of the original sample.

Bone graft materials of this invention that may be preferred are held together in surgically relevant shapes and sizes by foaming the inorganic reaction product with the collagen. The resulting articles retain substantially all of the biological and chemical properties of the shaped bodies taught in the '519 and '246 patents, while forming a shapeable, flexible unit dose. The bone graft materials may be manufactured into strips and cylinders of prescribed dimensions and volumes. The graft material will resorb following delivery in the surgical site and exhibit the same beneficial biological responses (e.g., bone formation) as the aforementioned shaped bodies.

In some embodiments, the bone graft materials may have up to about 30% by weight of biocompatible polymer. The biocompatible polymer may also be up to about 25% by weight in other embodiments. It will be appreciated that embodiments exist wherein the bone graft materials have up to about 20% or 10% by weight of a biocompatible polymer. In other embodiments where the polymer chosen is a collagen, the present invention exhibits a unique mineral (β-TCP) to collagen ratio that is unlike the ratios shared by other bone grafts. One skilled in the art may obtain bone graft materials of variable ratios depending on their particular needs. In one effective embodiment, the mass ratio of the reaction product and the collagen is 80:20. In others, it may be 90:10 or 70:30. The mass ratio may be altered without unreasonable testing using methods readily available in the art. It will be appreciated that this ratio is contrary to the mineral β-TCP to collagen ratios one skilled in the art would find in previous bone grafts while still maintaining all the properties (e.g., porosity, pore size distribution) that attribute to an effective bone graft (e.g., simultaneous bone formation, strength and graft resorption).

Due to the high porosity and broad pore size distribution (1 μm–1000 μm) of the present invention graft, the implant is not only able to wick/soak/imbibe materials very quickly, but is also capable of retaining them. A variety of fluids could be used with the present invention including blood, bone marrow aspirate, saline, antibiotics and proteins such as bone morphogenetic proteins (BMPs).

Materials of the present invention can also be imbibed with blood, cells (e.g. fibroblasts, mesenchymal, stromal, marrow and stem cells), protein rich plasma other biological fluids and any combination of the above. This capability has utility in cell-seeding, drug delivery, and delivery of biologic molecules as well as in the application of bone tissue engineering, orthopaedics, and carriers of pharmaceuticals.

Bone graft materials of the present invention that may be preferred exhibit high degrees of porosity. It is also preferred that the porosity occur in a broad range of effective pore sizes. In this regard, persons skilled in the art will appreciate that preferred embodiments of the invention may have, at once, macroporosity, mesoporosity, and microporosity. Macroporosity is characterized by pore diameters greater than about 100 μm and, in some embodiments, up to about 1000 μm to 2000 μm. Mesoporosity is characterized by pore diameters between about 100 μm and 10 μm, while microporosity occurs when pores have diameters below about 10 μm. It is preferred that macro-, meso-, and microporosity occur simultaneously and are interconnected in products of the invention. It is not necessary to quantify each type of porosity to a high degree. Rather, persons skilled in the art can easily determine whether a material has each type of porosity through examination, such as through the preferred methods of mercury intrusion porosimetry, helium pycnometry and scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

It will be appreciated that in some embodiments of materials prepared in accordance with this invention the overall porosity will be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, $1^{st}$ Ed., Hollowman, J. H., et al. (Eds.), Wiley & Sons, 1960, p. 409–417, who provides a formula for determination of porosity. Expressing porosity as a percentage yields pore volume. The formula is: Pore Volume=$(1-f_p)$ 100%, where $f_p$ is fraction of theoretical density achieved.

Porosity can be measured by Helium Pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume−measured volume)/apparent volume. Porosity and pore size distribution may also be measured by mercury intrusion porosimetry.

Pore volumes in excess of about 30% may be achieved in accordance with this invention while materials having pore volumes in excess of 50% or 60% may also be routinely attainable. Some embodiments of the invention may have pore volumes of at least about 70%. Some embodiments that may be preferred have pore volumes in excess of about 75%, with 80% being still more preferred. Pore volumes greater than about 90% are possible as are volumes greater than about 92%. In some preferred cases, such high pore volumes are attained while also attaining the presence of macro-, meso-, and microporosity as well as physical stability of the materials produced. It is believed to be a great advantage to prepare graft materials having macro-, meso-, and microporosity simultaneously with high pore volumes that also retain some compression resistance and flexibility when wetted.

In accordance with certain preferred embodiments of the present invention, a reactive blend in accordance with the invention may be imbibed into a material that is capable of absorbing it. It may be preferred that the material have significant porosity, be capable of absorbing significant amounts of the reactive blend via capillary action, and that the same be substantially inert to reaction with the blend prior to its autologous oxidation-reduction reaction. Due to this porosity, the bone graft materials disclosed herein may soak and hold fluids. Fluids would not be squeezed out as seen in other bone grafts found in the art. Some embodiments exhibit a wettability wherein bone graft material becomes fully saturated within 120 seconds with at least a 100% mass increase. In some embodiments, the graft material experiences a 150% mass increase and yet, in others, an approximate 200%–300% mass increase. Fluids that may be used in the present invention may be bone marrow aspirate, blood, saline, antibiotics and proteins such as bone morphogenetic proteins (BMPs) and the like.

Wettability determines the amount of fluid taken up by sample material and if the material absorbs an appropriate amount of fluid within a specified time. Pieces of the material are randomly selected, weighed, and placed in a container of fluid for 120 seconds. If the samples adequately take up fluid, they are then weighed again to determine the percentage of mass increase from fluid absorption.

In accordance with the present invention, some bone graft materials disclosed may be partially comprised of materials, or morsels, resulting from an oxidation-reduction reaction. These materials may be produced by methods comprising preparing an aqueous solution of a metal cation and at least one oxidizing agent. The solution is augmented with at least one soluble precursor anion oxidizable by said oxidizing agent to give rise to the precipitant oxoanion. The oxidation-reduction reaction thus contemplated is conveniently initiated by heating the solution under conditions of temperature and pressure effective to give rise to said reaction. In accordance with preferred embodiments of the invention, the oxidation-reduction reaction causes at least one gaseous product to evolve and the desired intermediate precursor mineral to precipitate from the solution.

The intermediate precursor mineral thus prepared can either be used "as is" or can be treated in a number of ways. Thus, it may be heat-treated greater than about 800° C. or, preferably, greater than about 1100° C. in accordance with one or more paradigms to give rise to a preselected crystal structure or other preselected morphological structures therein. In accordance with preferred embodiments, the oxidizing agent is nitrate ion and the gaseous product is a nitrogen oxide, generically depicted as $NO_{x(g)}$. It is preferred that the precursor mineral provided by the present methods be substantially homogenous. As used in this context, substantially homogenous means that the porosity and pore size distribution throughout the precursor mineral is the same throughout.

In accordance with other preferred embodiments, the intermediate precursor mineral provided by the present invention may be any calcium salt. Subsequent modest heat treatments convert the intermediate material to e.g. novel monophasic calcium phosphate minerals or novel biphasic β-tricalcium phosphate (β-TCP)+type-B, carbonated apatite (c-HAp) [$\beta\text{-}Ca_3(PO_4)_2 + Ca_5(PO_4)_{3-x}(CO_3)_x(OH)$] particulates. More preferably, the heat treatment converts the intermediate material to a predominantly β-TCP material.

It will be appreciated that the porosity is similar to that of inorganic shaped bodies disclosed in the '519 and '246 patents. The bone graft materials of the present invention are indeed improvements on the shaped bodies disclosed in the '519 and '246 patents. For some embodiments of the present invention, the shaped bodies of the '519 and '246 patents are modified using various natural and synthetic polymers, film forming materials, resins, slurries, aqueous mixtures, pre-polymers, organic materials, metals, and other adjuvants. Materials such as collagen, wax, glycerin, gelatin, polycaprolactone, pre-polymeric materials such as precursors to various nylons, acrylics, epoxies, polyalkylenes, and the like, were caused to permeate all or part of the shaped bodies formed in accordance with the '519 and '246 patents. The soak and hold properties of some graft materials disclosed herein exhibit at least a greater than 100% mass increase of blood. Many of the bone graft materials have a tough structural integrity with improved clinical handling when compared to the bodies of the '519 and '246 patents.

The bone graft materials may also have improved handling that can provide a unit dose delivery. The addition of a polymer in the present invention graft material greatly enhances the ability of the product to be shaped or cut without crumbling. The graft materials may be shaped or cut using various instruments such as a scapel or scissors. This feature finds utility in a variety of surgical applications, particularly since the bone graft can be formed "in situ" in an operating room to suit the needs of the patient in cases where the bone void to be filled is an irregular shape. Some graft materials disclosed may also be delivered into the bony site directly, shaped, and allowed to wick bodily fluids by an operator while during an operation.

The bone graft materials may be sterilized and may be preferably gamma irradiated at a range of about 25 kGy to 40 kGy.

Many of the embodiments disclosed herein are to fill bony voids and defects and may not be intrinsic to the stability of the surgical site. It will be appreciated that applications for the embodiments of the present invention include, but are not limited to, filling interbody fusion devices/cages (ring cages, cylindrical cages), placement adjacent to cages (i.e., in front cages), placement in the posterolateral gutters in posterolateral fusion (PLF) procedures, backfilling the iliac crest, acetabular reconstruction and revision hips and knees, large tumor voids, use in high tibial osteotomy, burr hole filling, and use in other cranial defects. The bone graft material strips may be suited for use in PLF by placement in the posterolateral gutters, and in onlay fusion grafting. Additional uses may include craniofacial and trauma procedures that require covering or wrapping of the injured/void site. The bone graft material cylinders may be suited to fill spinal cages and large bone voids, and for placement along the posterolateral gutters in the spine.

Figure 3B:
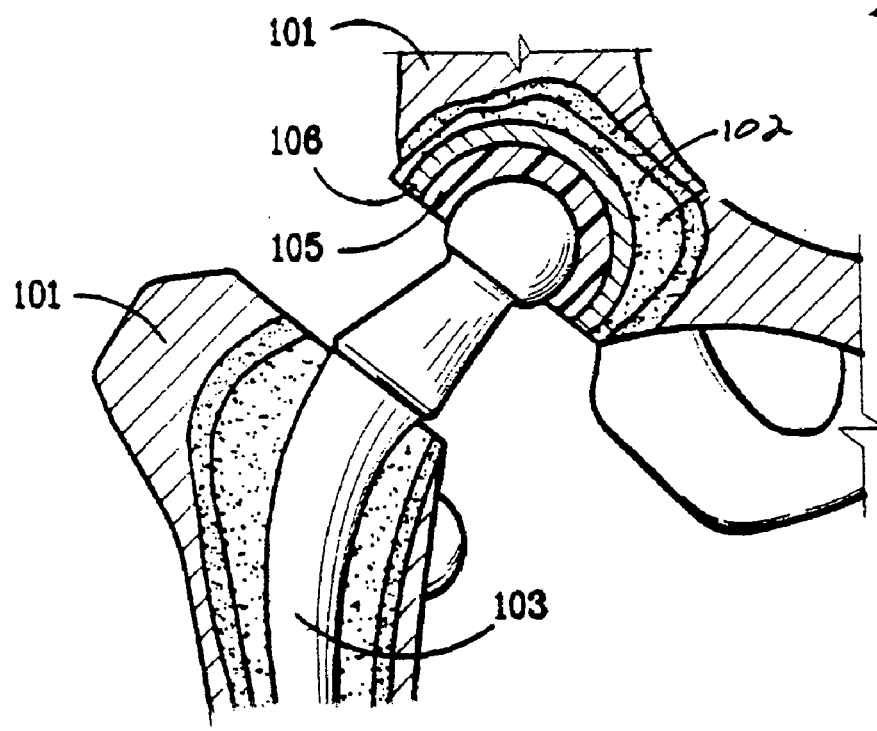
FIG. 3B depicts a semi-spherical form of the graft material 102 used to accommodate an artificial implant 103. The graft material 102 contains an acetabular cup 106, which holds a polyethylene cup 105, in this embodiment.
Figure 3A:
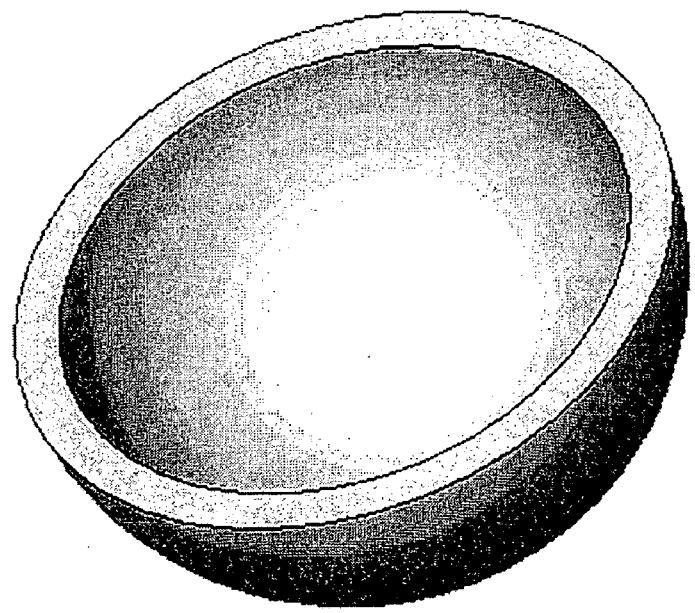
FIG. 3A illustrates one embodiment of the biocompatible graft material of the present invention in semi-spherical form used as a graft containment device.
Figure 4B:
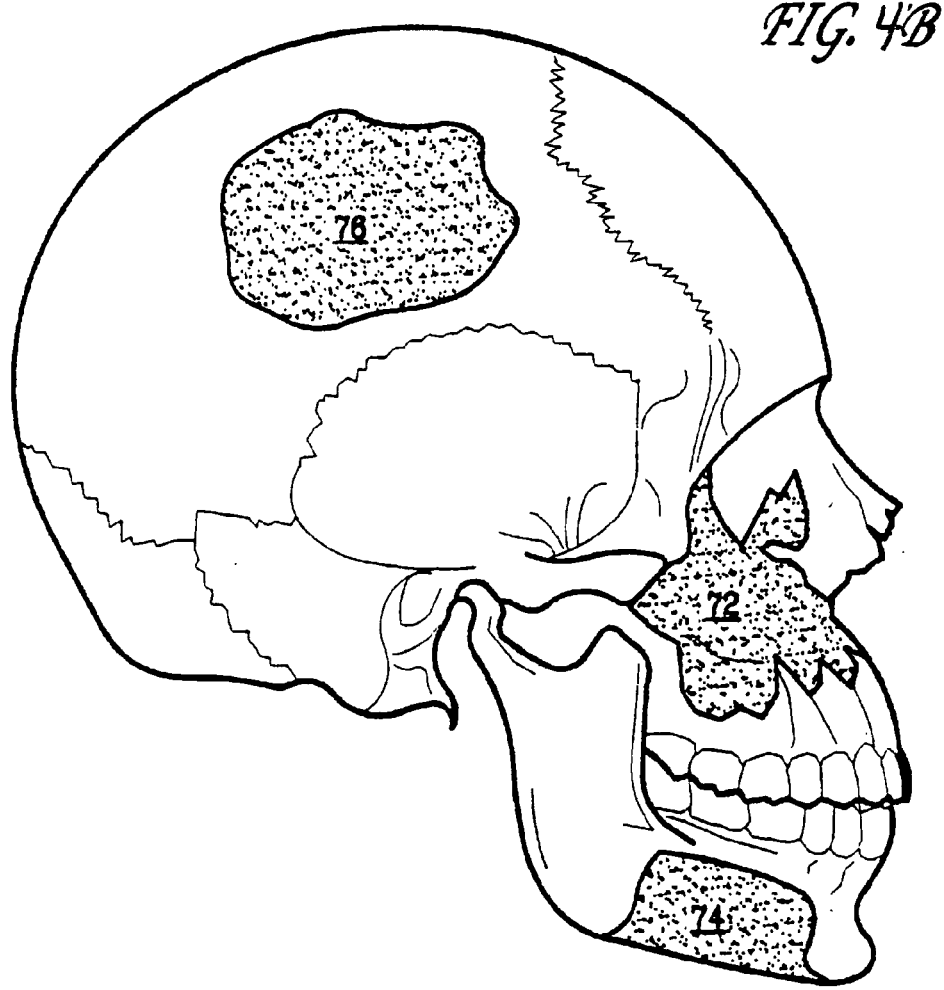
FIG. 4B illustrates another embodiment of the biocompatible graft material of the present invention used as a cranio-maxillofacial 76, zygomatic reconstruction 72, and mandibular implant 74.
Figure 4A:
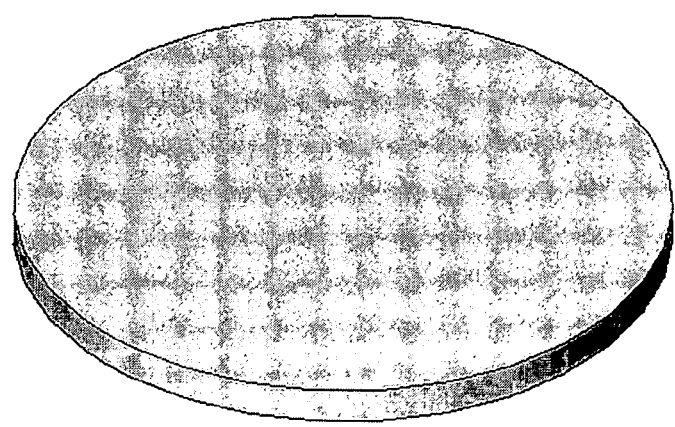
FIG. 4A illustrates the graft material of the present invention in disc form.
Figure 5:
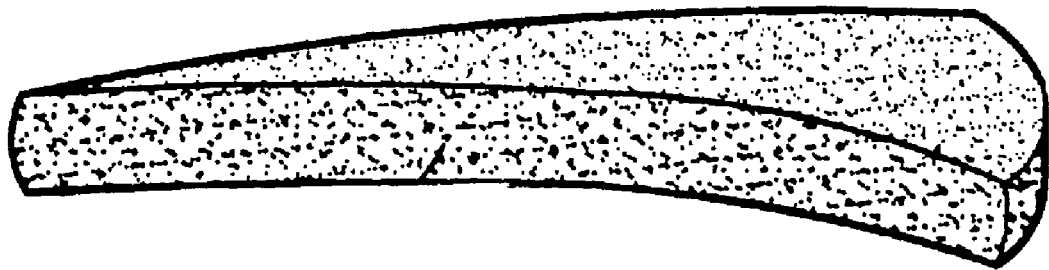
FIG. 5 illustrates one embodiment of a bone graft material described shaped into a block/wedge form and used as a tibial plateau reconstruction that is screwed, bonded, cemented, pinned, anchored, or otherwise attached in place.

Due to the wide range of applications for the embodiments of the present invention, it should be understood that the present invention graft material could be made in a wide variety of shapes and sizes via standard molding techniques. For instance, blocks and cylinders of the present invention may find utility in bone void filling and filling of interbody fusion devices; wedge shaped devices of the present invention may find utility in high tibial osteotomies; and strips may find utility in cranial defect repairs. Of particular interest, may be the use of some of the graft materials as semi-spherical (FIG. 3A), semi-tubular (FIGS. 7A–7C) or disc-shaped (FIG. 4A) strips for graft containment devices. An embodiment of the semi-spherical form 102 in use is depicted in FIG. 3B.

It will be appreciated that these shapes are not intended to limit the scope of the invention as modifications to these shapes may occur to fulfill the needs of one skilled in the art. The benefits of the graft containment materials that, for instance, may be used in acetabular reconstruction made from the present invention are several-fold. The graft materials may act as both a barrier to prevent migration of other implants or graft materials and serves as an osteoconductive resorbable bone graft capable of promoting bone formation. The graft containment device may be relatively non-load bearing, or partially load bearing, or may be reinforced to be fully load bearing as described below. Depending on the form, the graft materials have barrier properties because it maintains its structural integrity.

Figure 6A:
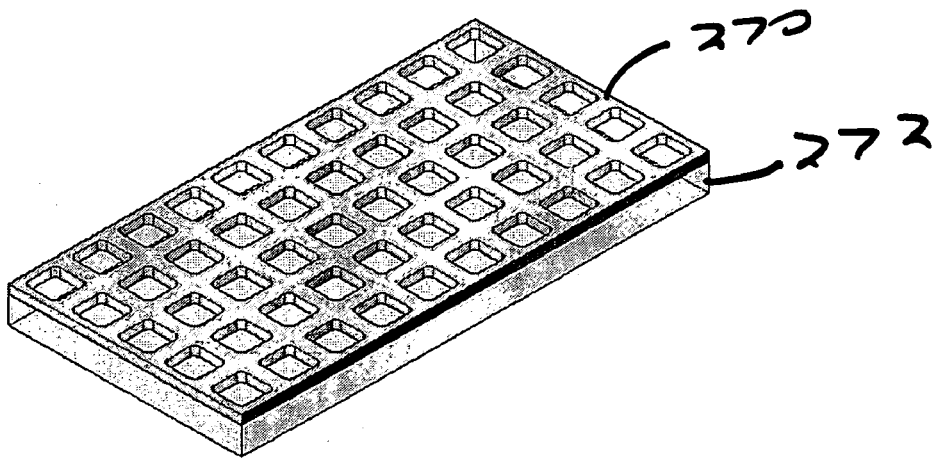
FIGS. 6A and 6B illustrate synthetic resorbable defect filling bone graft materials 272 for bone restoration having mesh 270 attached to one side.
Figure 6B:
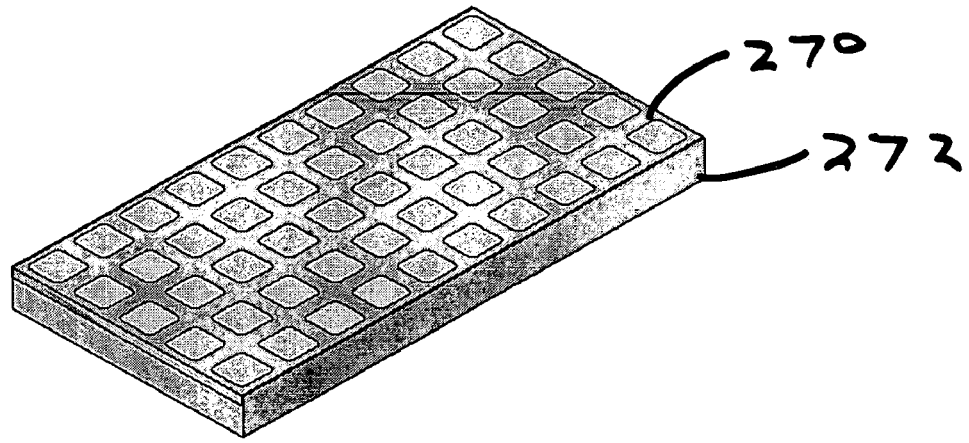
Figure 6C:
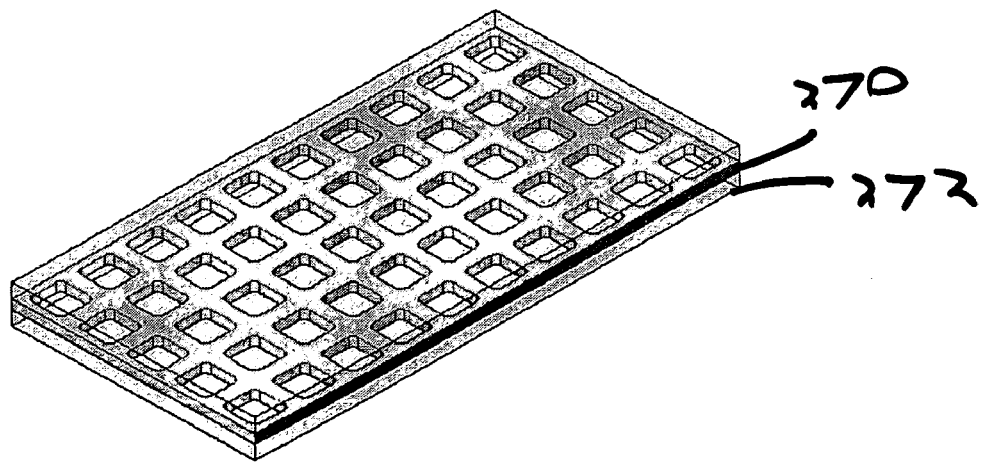
FIG. 6C depicts a synthetic resorbable defect filling bone graft material block in which the mesh 270 is sandwiched between the graft material 272.
Figure 7A:
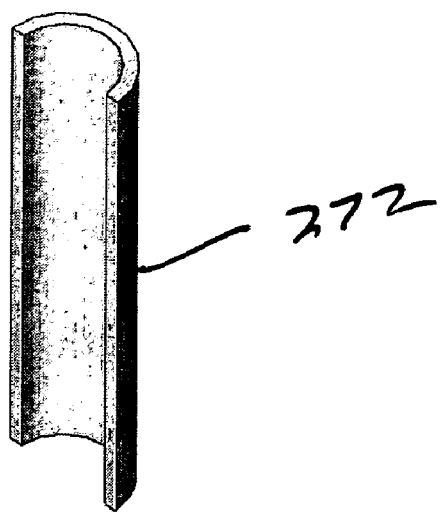
FIGS. 7A, 7B, and 7C illustrate an embodiment of the biocompatible graft material of the present invention in semi-tubular form used as a long bone reinforcement sleeve. As shown in the figures, the semi-tube may have a moon cross-section with a uniform thickness (FIG. 7A); or a crescent moon cross-section with a tapered radius that comes to a point (FIG. 7B) or a tapered radius that is rounded on the edges (FIG. 7C).
Figure 7B:
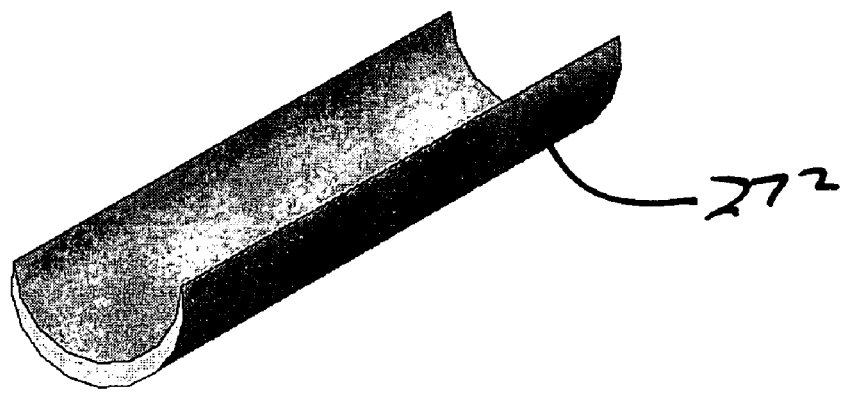
Figure 7C:
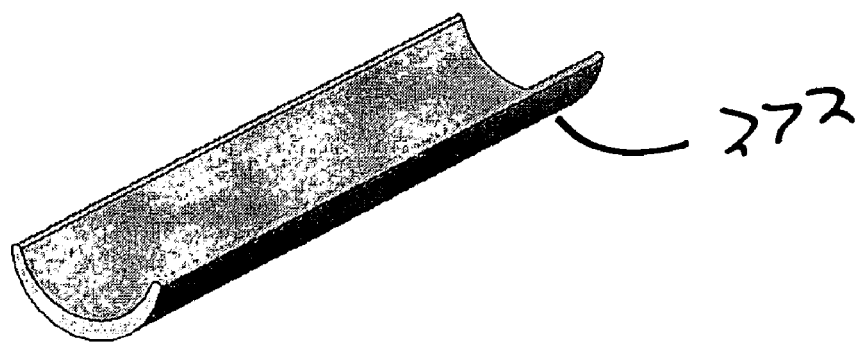

In applications requiring graft materials with load bearing capabilities, the graft materials of the present invention may have meshes or plates affixed. The meshes or plates may be of metal, such as titanium or stainless steel, or of a polymer or composite polymer such as polyetheretherketone (PEEK), or nitinol. As depicted in FIGS. 6A and 6B, a metallic mesh 270 may be placed to one side of the bone graft material 272 to add strength and load bearing properties to the implant. In FIG. 6A, the mesh plate 270 sits affixed to one surface of the graft material 272. In FIG. 6B, the mesh plate 270 penetrates one surface of the graft material 272 with one side of mesh exposed on top. In FIG. 6C, the mesh plate 270 is immersed more deeply than in FIG. 6B within the graft material 272. FIGS. 7A–7C depict another embodiment of the graft material 272 in semi-tubular form. A mesh may be affixed to a surface for further support in long bone reinforcement. Due to the unique properties of the present invention graft material, the mesh may be affixed in the body using sutures, staples, screws, cerclage wire or the like.

One skilled in the art may place the mesh in any location necessary for a selected procedure in a selected bodily void. For instance, a composite of mesh and graft material could be used in a craniomaxillofacial skull defect with the more pliable graft surface being placed in closer proximity to the brain and the more resilient mesh surface mating with the resilient cortical bone of the skull. In this manner, the mesh or plate may be affixed to one side of the graft material. Alternatively, the mesh or plate may be affixed to both sides of the graft material in sandwich fashion. Likewise, graft material could be affixed to both sides of the mesh or plate.

In some embodiments, the mesh may be immersed within the graft material. The meshes may be flat or may be shaped to outline the graft material such as in a semi-spherical, semi-tubular, or custom form. These embodiments may be unique due to their integral relation between the graft material and the mesh. This is contrary to other products in the field in which the graft material is placed adjacent to the structural implant or, in the case of a cage, within the implant.

In accordance with the present invention, another embodiment provides a bone graft for long bone reinforcement comprising a biocompatible, resorbable semi-tubular shape, or sleeve, of a polymer and beta-tricalcium phosphate, the graft having interconnected macro-, meso-, and microporosity. A mesh may be affixed to the surface of the sleeve or may be immersed in the sleeve. The mesh may be made of titanium, stainless steel, nitinol, a composite polymer, or polyetheretherketone. In some embodiments that may be preferred, the polymer may be collagen. The beta-tricalcium phosphate and polymer may be in a mass ratio of about 90:10 to about 70:10, or about 85:15 to about 75:25. The cross-section of the sleeve may be in the shape of a crescent shape moon (FIG. 7B).

In other embodiments, there is a graft for the restoration of bone in the form of a shaped body, the shaped body comprising a polymer and beta-tricalcium phosphate, the material of the graft having interconnected macro-, meso-, and microporosity; the body shape being selected to conform generally to a mamalian, anatomical bone structure. The shapes will vary depending on the area of the body being repaired. Some basic shapes may be a disk, semi-sphere, semi-tubular, or torus. In some embodiments, the shape will conform generally to the acetabulum.

Other graft materials of the present invention having load-bearing capabilities may be open framed, such that the bone graft material is embedded in the central opening of the frame. The frame may be made of a metal such as titanium or of a load-bearing resorbable composite such as PEEK or a composite of some form of poly-lactic acid (PLA). In the case of the latter, the acid from the PLA co-acts, or interacts with the calcium phosphate of the embedded bone graft material to provide an implant with superior resorption features.

The graft materials can also be imbibed with any bioabsorbable polymer or film-forming agent such as polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), polyesters and the like. The resultant graft material is strong, carveable, and compressible. The grafts of the present invention coated with agents such as the aforementioned may still absorb blood.

In another embodiment of the present invention, the graft materials may be used as an attachment or coating to any orthopaedic implant such as a metal hip stem, acetabular component, humeral or metatarsal implant, vertebral body replacement device, pedicle screw, general fixation screw, plate or the like. The coating may be formed by dipping or suspending the implant for a period of time in a substantially homogenous slurry of polymer and mineral and then processing via freeze-drying/lypholization and crosslinking techniques. As used in this context, substantially homogenous means that the ratio of elements within the slurry is the same throughout. Alternatively, a female mold may be made of the implant and the slurry may be poured into the mold and processed, as described above, to form the coating.

In yet another embodiment of the present invention, the graft material may be shredded or cut into small pieces. These smaller shredded pieces could then be used as filler or could be placed in a syringe body. In this fashion, fluids could be directly aspirated into or injected into the syringe body thereby forming a cohesive, shapeable bone graft mass "in situ" depending upon the application requirements. The shredded pieces find particular use as filler for irregular bone void defects. Further, unlike traditional bone graft substitutes they are highly compressible and therefore can be packed/impacted to insure maximum contact with adjacent bone for beneficial healing.

It will be appreciated that methods of treating bony defects are foreseen by the embodiments of the present invention. A method for restoring or repairing bone in an animal comprising accessing a site to be restored; and implanting into a bony space a bone graft material comprising biocompatible, resorbable collagen, the oxidation-reduction reaction product of at least one metal cation, at least one oxidizing agent, and at least one oxidizable precursor anion. The graft material used in this method may be chosen by one skilled among those disclosed in the present application.

EXAMPLES

Example 1

One embodiment was comprised of β-TCP, with a cation to anion ratio of $Ca_3(PO_4)_2$; and medical grade Type I bovine collagen, manufactured in the following manner. Inorganic scaffolds were made using the RPR process disclosed in U.S. Pat. Nos. 5,939,039 and 6,325,987. The resultant inorganic scaffolds were crushed and sieved to obtain morsels in the size range of 0.25 mm–4 mm. The morsels were added to a fibrous collagen slurry in a wet processing room and the resultant slurry was further mixed and casted/molded into various shapes in a cleanroom. The shapes were freeze-dried and crosslinked using Dehydrothermal (DHT) treatment to produce resultant bone graft material shaped products.

Example 2

Mineral Component of Bone Graft Material

Approximately 78%–82% by weight of some bone graft materials of the present invention is β-TCP, with the cation to anion ratio of $Ca_3(PO_4)_2$. Each lot of the mineral component of these bone graft materials was tested using X-ray diffraction (XRD) to confirm phase pure β-TCP in accordance with ASTM F1088-87, Standard Specification for Beta-Tricalcium Phosphate for Surgical Implantation. In addition to XRD, Inductively Coupled Plasma Chromatography (ICP) was used to demonstrate that the levels of heavy metals in the predicate bone graft material are below those established in ASTM F-1088-87. Fourier Transform Infrared Spectroscopy (FTIR) analyses of the bone graft material were also performed.

Figure 8:
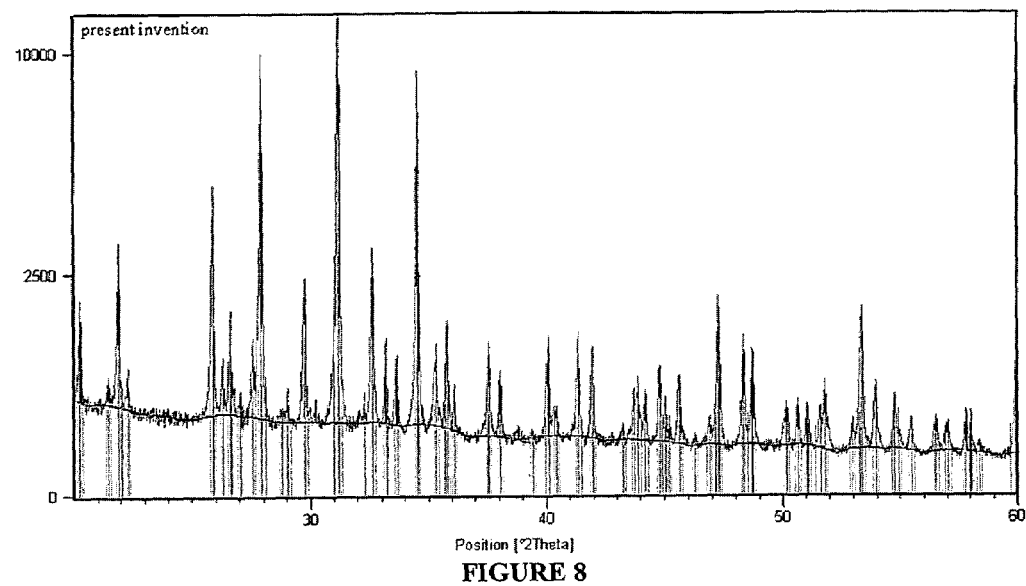
FIG. 8 is a representative XRD spectra of a bone graft material of the present invention (top) vs. β-TCP (bottom).
Figure 9:
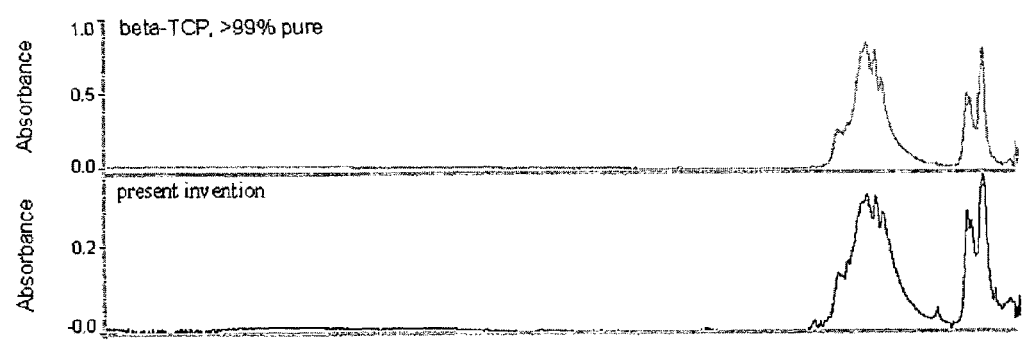
FIG. 9 is a representative FTIR spectrum of bone graft material of the present invention vs. β-TCP (beta-TCP).

The quantitative XRD results show that the mineral component of the bone graft material is 98.25% pure β-TCP, which matches well with the ICDS standard plot for β-TCP pictured with the representative XRD pattern of the bone graft material (FIG. 8). The ICP results for the bone graft material show that the levels of heavy metal contaminants—arsenic (As), cadmium (Cd), mercury (Hg), and lead (Pb), are below the method detection limits of 2.25 ppm, 1.80 ppm, 2.25 ppm and 4.5 ppm, respectively, thus below the limits set forth in ASTM F-1088-87. Qualitative FTIR results show a 95% match of the bone graft material to greater than 99% pure β-TCP. A representative FTIR spectrum is shown in FIG. 9.

Example 3

Bulk Density

Bulk density of bone graft material was calculated from three representative samples. Each sample was measured in triplicate to provide an average calculated density of 0.46 g/cc+/−0.03 g/cc.

Example 4

Porosity and Pore Size Distribution

In one embodiment of the present invention, as determined by mercury intrusion porosimetry, pore diameters in the graft range from 1 μm to 1000 μm. Approximately 5% to 15% of the pores are greater than 100 μm, approximately 50%–70% of the pores are between 10 μm–100 μm, and approximately 20%–35% of the pores are less than 10 μm. The larger macro pores (greater than 100 μm) allow bone to grow in apposition to the calcium phosphate surfaces of the implant. The smaller meso (10 μm–100 μm) and micro (less than 10 μm) interconnected pores allow for fluid communication and nutrient transport. Total porosity is approximately 70%–80%.

Example 5

Scanning Electron Microscopy Evaluation

Figure 10:
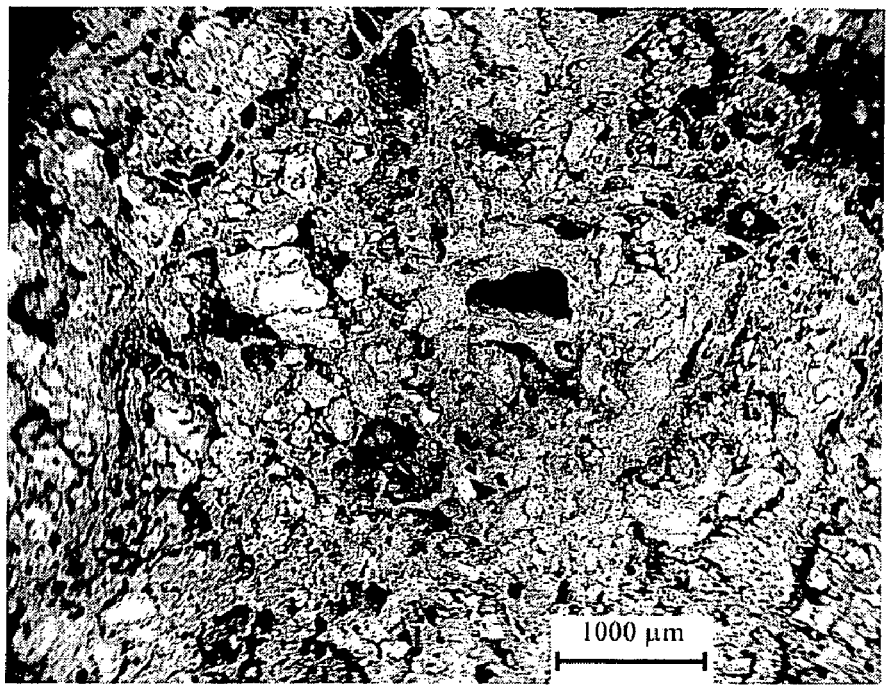
FIG. 10 is an SEM of the bone graft material, 20×.
Figure 11:
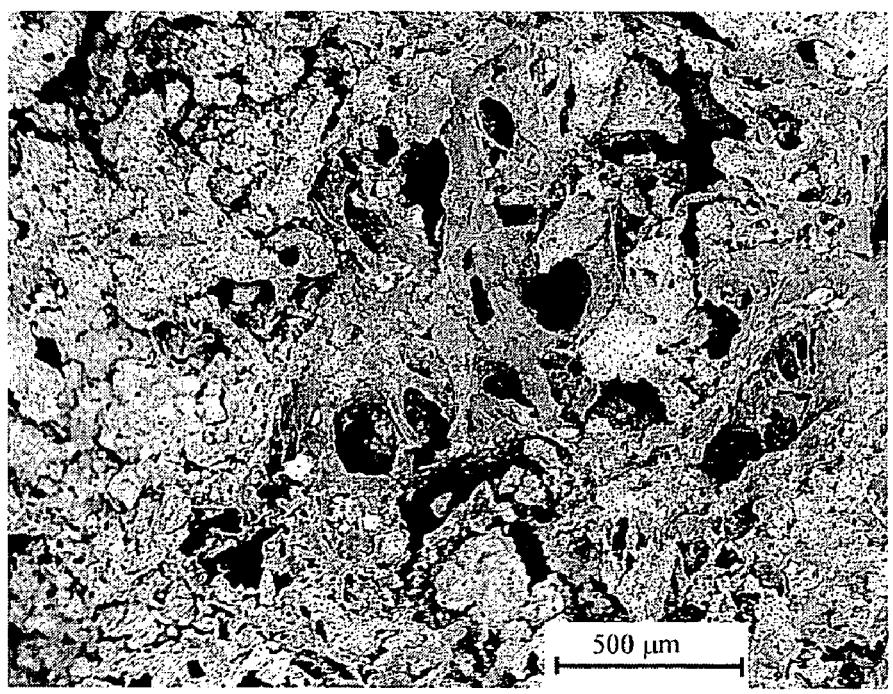
FIG. 11 is an SEM of the bone graft material, 50×.
Figure 12:
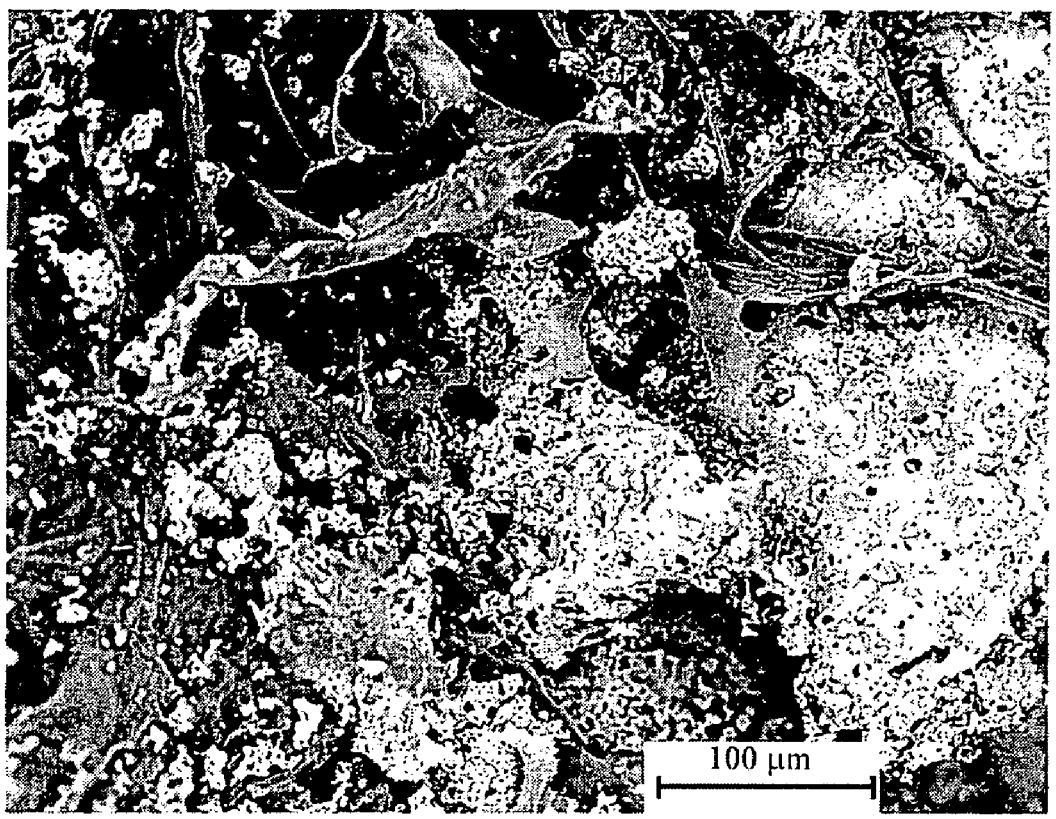
FIG. 12 is an SEM of the bone graft material, 250×.
Figure 13:
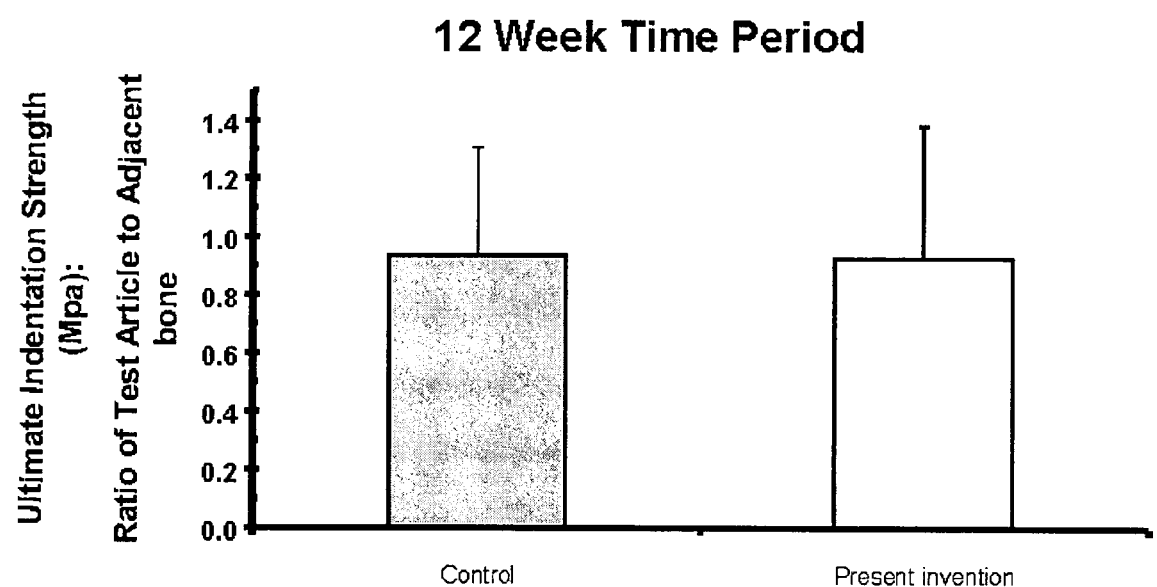
FIG. 13 depicts the Ultimate Indentation Strength for one embodiment of the bone graft material vs. control normalized by adjacent bone at 12 weeks.

Scanning electron micrographs (SEM) of one embodiment of the present invention graft material are provided in FIGS. 10, 11, and 12.

Example 6

In-Vivo

A GLP animal study was performed at North American Science Associates, Inc. (NAMSA), Northwood, Ohio, to evaluate the biological effects of the bone graft material and a control in metaphyseal defects of adult dogs. Sixteen dogs were implanted both with one embodiment of the present invention and the control. Animals were sacrificed at each of the time periods of 3, 6, 12, and 24 weeks. Gross evaluation, radiographic assessment, histological evaluation, histomorphometry, and mechanical evaluations were performed.

In this animal study, the control was placed in the proximal humerus, and the present invention was placed in the femoral condyle.

Quantitative Histology

Qualitatively, by 12 weeks approximately 80%–90% of the bone graft material implant was resorbed and the amount of new bone in the implant was approximately 20%–25%. For the predicate (control) at 12 weeks, approximately 80%–90% of the implant was resorbed and the amount of new bone in the implant was approximately 30%–35%. By 24 weeks, the estimated amount of new bone in the implant was approximately 25–35% for both, with equivalent resorption of each material.

Mechanical Evaluation

In addition to histology, half of each specimen from the animal study was utilized for biomechanical indentation testing. In brief, a flat-head indentor with a diameter equal to half the diameter of the defect (e.g., 5 mm diameter indentor for 10 mm humeral defects and 4 mm diameter indentor for 8 mm femoral condyle defects) was lowered (compressed) into the center of the defect in order to evaluate the structural properties of the repaired defect at 3, 6, 12, and 24-week time points. For comparison purposes, the indentor was also lowered in an area adjacent to the defect to evaluate the structural properties of the adjacent bone. Ultimate indentation load, yield load, stiffness, and ultimate indentation strength were quantified.

By twelve weeks, strength between the bone graft material and control was similar, and not significantly different. In addition, the strength and stiffness of each material at this time point were statistically similar to the respective adjacent bone.

The similarities in strength and stiffness between the bone graft material repaired defect site and the control repaired defect site are readily apparent after normalization with the adjacent bone.

Example 7

Gelatin Modification

A piece of the inorganic material was immersed in a solution prepared by dissolving 7.1 g food-grade gelatin (CAS #9000-70-0) (Knox Unflavored Gelatin, Nabisco Inc., East Hanover, N.J. 07936) in 100.0 g deionized water at approximately 90° C. The inorganic material readily imbibed the warm gelatin solution and, after several minutes, the largely intact piece of inorganic material was carefully removed from the solution and allowed to cool and dry overnight at room temperature. The gelatin solution gelled on cooling and imparted additional strength and improved handling properties to the inorganic material. Although no pH or electrolyte/nonelectrolyte concentration adjustments were made to the system described in this example, it is anticipated that such adjustments away from the isoelectric point of the gelatin would impart additional rigidity to the gelatin gel and, thereby, to the gelatin-treated inorganic material. Significant additional strength and improved handling properties were noted in the gelatin-treated inorganic material after the gelatin was allowed to thoroughly dry for several days at room temperature. Some shrinkage of the gelatin-treated inorganic materials was noted on drying. The shrinkage was nonuniform with the greatest contraction noted near the center of the body. This central region was, of course, the last area to dry and, as such, was surrounded by hardened inorganic material which could not readily conform to the contraction of the core as it dehydrated. The material exhibited considerable improvement in compression strength and a dramatically reduced tendency to shed particulate debris when cut with a knife or fine-toothed saw. It is presumed that the film-forming tendency of the gelatin on drying induced compressive forces on the internal cellular elements of the inorganic sponge material, thereby strengthening the overall structure.

Cylindrical plugs could be cored from pieces of the air dried gelatin-treated inorganic material using hollow punch tools ranging from ½ inch down to ⅛ inch in diameter.

Figure 14:
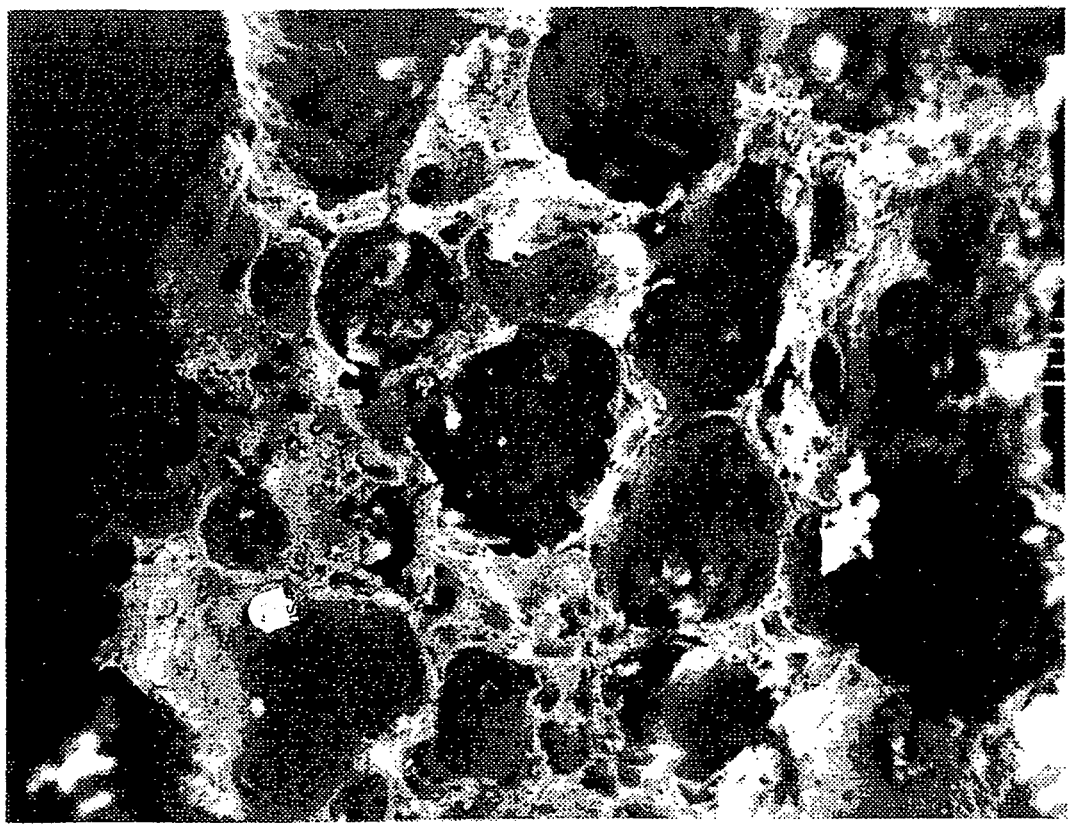
FIG. 14 is an SEM of air-dried gelatin treated inorganic material, 23×.
Figure 15:
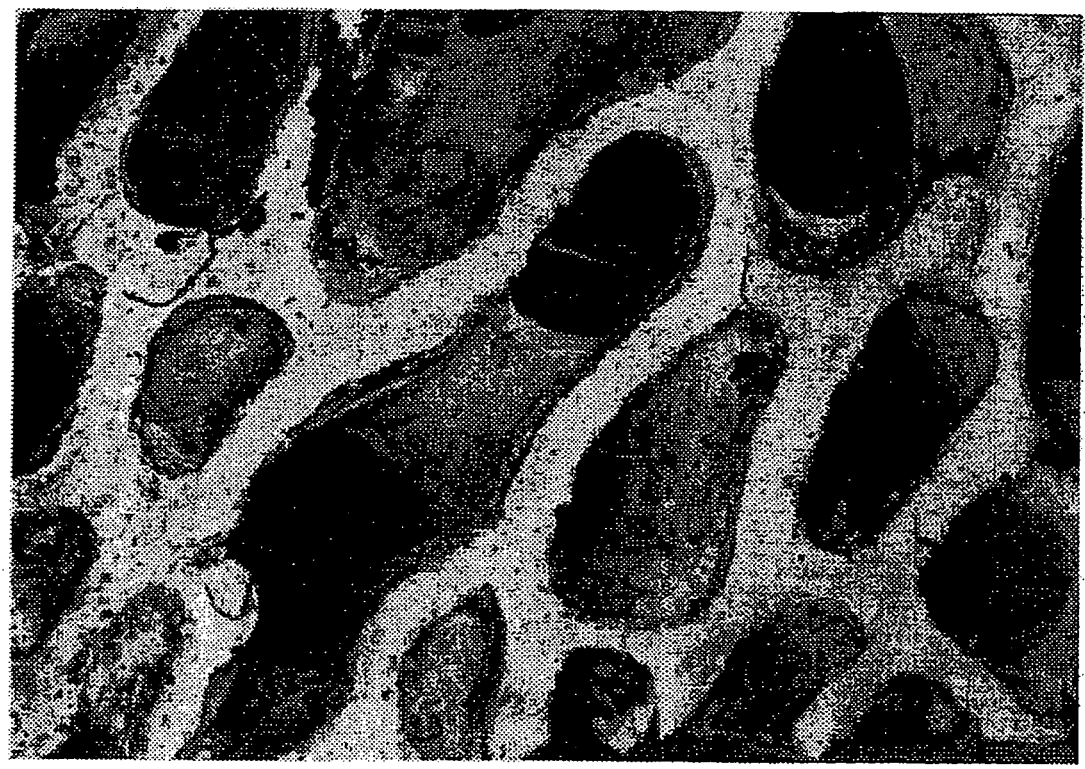
FIG. 15 is an SEM of sheep trabecular bone, 25×.
Figure 16:
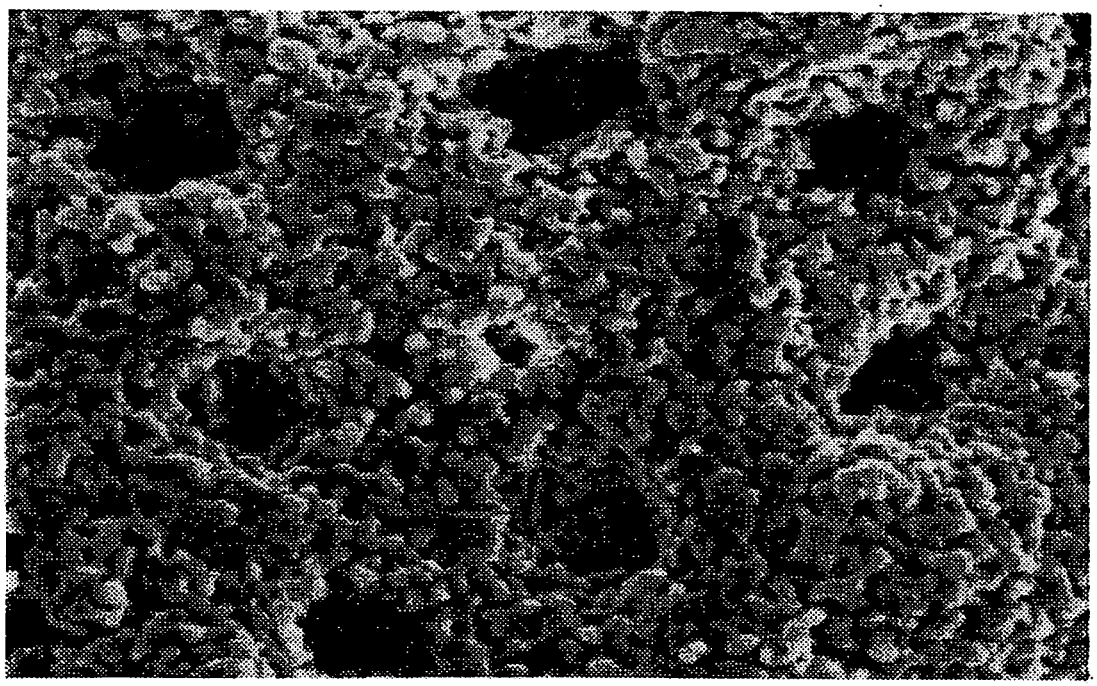
FIG. 16 is an SEM of the material shown in FIG. 14, 2000×.

FIG. 14 is a SEM of the air-dried gelatin treated inorganic material. FIG. 15 is a SEM of sheep trabecular bone. The highly porous macrostructure of sheep trabecular bone is representative of the anatomical structure of cancellous bone of higher mammals, including humans. The sample of sheep trabecular bone was prepared for SEM analysis by sputter coating a cross-sectional cut from a desiccated sheep humerus. FIG. 16 is a higher magnification SEM of the air-dried gelatin treated inorganic material depicted in FIG. 14. From this SEM micrograph, the presence of meso- and microporosity in the calcium phosphate matrix is readily apparent.

Example 8

Sterilization

Samples of gelatin-treated inorganic material were prepared as described in Example 7 and allowed to thoroughly dry at room temperature for longer than one week. Pieces of this dry gelatin-treated material were subjected to prolonged oven treatments in an air atmosphere within a Vulcan model 3-550 oven to simulate conditions typically encountered in "dry heat" sterilization procedures. The following table summarizes these experiments

| Temperature (° C.) | Time (h) | Observations |
| --- | --- | --- |
| 130 | 3 | No color change |
| 130 | 6 | Very slight yellowing |
| 130 | 15 | Very slight yellowing |
| 150 | 4 | Very slight yellowing |
| 170 | 1 | Very slight yellowing |
| 170 | 3.5 | Pale yellow at surface, white interior |

It was assumed that temperature equilibration between the samples and the oven was rapidly attained due to the significant porosity and low thermal mass of the materials. Clearly, there was no significant degradation of the gelatin under these heat treatment regimens. Furthermore, a subjective assessment of the strength of these dry heat treated specimens showed no apparent changes.

Example 9

Template Residues

A reactant solution was prepared as described in the '162 patent. A variety of shapes, including disks, squares, and triangles, were cut from a sheet of 3/32 inch thick sponge material (Spontex, Inc., P.O. Box 561, Santa Fe Pike, Columbia, Tenn. 38402) using either scissors or hollow punches. The cut pieces of compressed sponge were fully imbibed with the reactant solution after which they swelled to form cylinders, cubes, and wedges. These solution saturated sponge articles were placed into an oven preheated to 500° C. and held at that temperature for 1 hour. After cooling, the inorganic sponge pieces were carefully removed from the considerable amount of crusty white solid resulting from the exudate material. All samples had been converted to an inorganic replica of the original organic sponge structures. The vestigial structures represented positive versions of the original sponge structures with faithful replication of the cellular elements and porosity. The vestigial masses were fragile with very low apparent density, but they were robust enough to be handled as coherent blocks of highly porous solid once they were removed from the exudate material. After refiring the samples between 800° C. to 1100° C.

(Vulcan furnace) for 15 minutes, the final inorganic sponge samples were completely white. The integrity of the various samples made from the controlled porosity cellulose sponge was improved over corresponding samples prepared from the commercial cellulose sponge materials. The samples were then crushed and sieved to obtain morsels in the size range of 0.25 mm–4 mm. The morsels were added to a collagen slurry in a wet processing room and the resultant slurry was further mixed and casted/molded into various shapes in a cleanroom. The shapes were freeze-dried and crosslinked to produce resultant bone graft material shaped products.

Example 10

Modified Templates

Pieces of an inorganic sponge material were immersed in a gelatin solution prepared as described in Example 7 except that 7.1 g of Knox gelatin was dissolved in 200 g deionized water rather than 100 g of deionized water. The inorganic sponge material readily imbibed the warm gelatin solution and, after several minutes, the largely intact pieces of inorganic sponge material were carefully removed from the solution and allowed to cool and dry at room temperature. Significant additional strength and improved handling properties were noted in the gelatin-treated inorganic sponge material after the gelatin was allowed to thoroughly dry for several days. The material exhibited considerable improvement in compression strength and a dramatically reduced tendency to shed particulate debris when cut with a knife or fine-toothed saw.

Several pieces of gelatin treated sponge which had been drying in air for over 1 week were subjected to a burnout of the organic material at 800° C. (Vulcan furnace) for 30 minutes. The snow white inorganic sponge samples were weighed after firing and it was determined that the level of gelatin in the treated samples was 13.8+/−1.0 wt % (with respect to the inorganic sponge material).

Example 11

Rewetting

Several pieces of air-dried gelatin-treated inorganic sponge material from Example 7 were placed in deionized water to assess the rewetting/rehydration behavior. Initially, the pieces floated at the water surface but, after approximately 2 hours, the sponge pieces began to float lower in the water indicating liquid uptake. After 24 hours, the samples were still floating, but greater than 50% of the sponge volume was below the liquid surface. After 48 hours, the inorganic sponge samples were completely submerged suggesting complete rehydration of the gelatin and complete water ingress into the structure via interconnected porosity.

Example 12

Shaped Calcium Phosphates

Several pieces of the inorganic sponge material made from U.S. Pat. Nos. 5,939,039 and 6,325,987 were immersed in a 50 wt % solution of disodium glycerophosphate hydrate in 10.0 g deionized water. The inorganic sponge material readily imbibed the disodium glycerophosphate solution and, after several minutes, the largely intact pieces of saturated inorganic sponge material were carefully removed from the solution. The wetted pieces were placed in a Vulcan model 3-550 oven preheated to 150° C. Immediately, temperature was ramped to 850° C. followed by a 60 minute hold. After cooling to room temperature, the surface of the treated inorganic sponge material had a glassy appearance, and significant additional strength and improved handling properties were noted. Upon examination of the pieces with a Leica™ zoom stereo microscope, the presence of a glassy surface was confirmed and rounding of the features was evident indicating that some level of sintering had occurred. Considerable shrinkage of the pieces was also noted.

Example 13

Discoid Bodies

A reactant solution was prepared as described in the '519 patent. Disks were cut from a sheet of 3/32 inch thick compressed sponge using a 3/8 inch diameter hollow punch and a model No. 3393 Carver hydraulic press (Carver Inc., 1569 Morris St., P.O. Box 544, Wabash, Ind. 46992) to ensure uniform sizing. The disks were distended by immersion in deionized water and the resulting sponge cylinders, each approximately 3/8 inch diameter by 1 inch length, were then blotted on paper towel to remove as much excess water as possible. The damp sponge cylinders were then imbibed with approximately seven times their weight of the reactant liquid. Nine of the solution imbibed pieces were placed horizontally and spaced uniformly in a 100 mm×20 mm Pyrex petri dish. Two petri dishes, containing a total of 18 imbibed sponge cylinders, were irradiated for a total of two minutes. After 30 seconds of exposure, the reactant liquid, which had exuded from the sponge cylinders, had reacted/dehydrated to form a crusty white deposit in the petri dishes. After several additional cycles of exposure, the fully dried sponge cylinders were removed. The dried, solid-filled cylindrical sponge pieces were arrayed in a rectangular alumina crucible (2½" W×6" L×½" D) and placed in a furnace preheated to 500° C. The furnace temperature was ramped at 40° C./minute to 800° C. and held at 800° C. for 45 minutes. The resultant cylindrical white porous inorganic sponge samples were robust and exhibited strengths qualitatively similar to those attained from the fully dried gelatin-treated samples prepared as described in Example 10.

What is claimed is:

1. A biocompatible bone graft material comprising a homogenous composite of biocompatible, resorbable collagen and calcium phosphate, the biocompatible bone graft having macro-, meso-, and microporosity.

2. The bone graft material of claim 1 wherein said collagen is Type I bovine collagen.

3. The bone graft material of claim 1 wherein said phosphate and collagen have a mass ratio of about 90:10 to about 70:30.

4. The bone graft material of claim 3 wherein said phosphate and collagen have a mass ratio of about 85:15 to about 75:25.

5. The bone graft material of claim 1 having up to about 30% by weight of collagen.

6. The bone graft material of claim 1 having up to about 20% by weight of collagen.

7. The bone graft material of claim 1 having up to about 10% by weight of collagen.

8. The bone graft material of claim 1 wetted with a fluid comprising bone marrow aspirate, blood, or saline.

9. The bone graft material of claim 1 having a cylindrical, block, or discoid shape.

10. The bone graft material of claim 9 also comprising a metal mesh.

11. The bone graft material of claim 10 wherein said metal comprises titanium.

12. The bone graft material of claim 1 wherein the bone graft material is shredded.

13. A bone graft for long bone reinforcement in the form of a sleeve, the graft comprising a homogenous composite of biocompatible, resorbable collagen and calcium phosphate, the graft having macro-, meso-, and microporosity.

14. The bone graft of claim 13 further comprising a mesh affixed to a surface of the sleeve.

15. The bone graft of claim 14 wherein said mesh is immersed in the graft.

16. The bone graft of claim 14 wherein the mesh is of titanium, stainless steel, nitinol, a composite polymer, or polyetheretherketone.

17. The bone graft of claim 13 wherein the calcium phosphate and collagen are in a mass ratio of about 90:10 to about 70:10.

18. The bone graft of claim 13 wherein the calcium phosphate and collagen are in a mass ratio of about 85:15 to about 75:25.

19. The bone graft of claim 13 wherein the cross-section of the sleeve is in the shape of a crescent shape moon.

20. The bone graft of claim 13 wherein the calcium phosphate is beta-tricalcium phosphate.

21. A graft for the restoration of bone in the form of a shaped body, the shaped body comprising a homogenous composite of polymer and beta-tricalcium phosphate, the graft having interconnected macro-, meso-, and microporosity; the shaped body being selected to conform generally to a mammalian, anatomical tissue structure; and further comprising a mesh affixed to a side of the composite.

22. The graft of claim 21 wherein the mesh is of titanium, stainless steel, nitinol, a composite polymer, or polyetheretherketone.

23. The graft of claim 21 wherein the polymer is collagen.

24. The graft of claim 21 wherein the body shape is a disk, semi-sphere, semi-tubular, or torus.

25. The graft of claim 21 wherein the body shape conforms to the acetabulum.

26. The graft of claim 21 wherein the beta-tricalcium phosphate and polymer are in a mass ratio of about 90:10 to about 70:10.

27. The graft of claim 26 wherein the beta-tricalcium phosphate and polymer are in a mass ratio of about 85:15 to about 75:25.

* * * * *